United States Patent
Baumann et al.

(10) Patent No.: US 7,521,459 B2
(45) Date of Patent: Apr. 21, 2009

(54) METHOD FOR TREATING DAMAGED SKIN

(75) Inventors: Leslie Baumann, Miami Beach, FL (US); Esperanza Welsh, Miami Beach, FL (US)

(73) Assignee: Metabeauty Inc., Miami Beach, FL (US)

( * ) Notice: Subject to any disclaimer, the term of this patent is extended or adjusted under 35 U.S.C. 154(b) by 370 days.

(21) Appl. No.: 10/627,994

(22) Filed: Jul. 28, 2003

(65) Prior Publication Data

US 2004/0087614 A1    May 6, 2004

(51) Int. Cl.
*A61K 31/4188* (2006.01)
*C07D 471/04* (2006.01)
*C07D 471/14* (2006.01)

(52) U.S. Cl. .................... 514/293; 546/118
(58) Field of Classification Search ............ 514/292, 514/293
See application file for complete search history.

(56) References Cited

U.S. PATENT DOCUMENTS

| | | | |
|---|---|---|---|
| 4,689,338 | A | 8/1987 | Gerster |
| 5,238,944 | A | 8/1993 | Wick et al. |
| 6,147,086 | A | 11/2000 | Brenman |
| 6,335,023 | B1 | 1/2002 | Yu et al. |
| 2004/0180919 | A1* | 9/2004 | Miller et al. ............ 514/291 |
| 2004/0248837 | A1 | 12/2004 | Raz et al. |

FOREIGN PATENT DOCUMENTS

WO    WO 00/40228    7/2000

OTHER PUBLICATIONS

U.S. Appl. No. 10/178,082, filed Apr. 2003, Maibach et al.*
Stockfleth et al., "Successful Treatment of actinic keratosis with imiquimod cream 5%: a report of six cases" (2001) British Journal of Dermatology, vol. 144, pp. 1050-1053.*
Silverman, R. B., "The Organic Chemistry of Drug Design and Drug Action," published 1992 by Academic Press, pp. 69-70.*
Izumi, T., et al.; 1H-Imidazo[4,5-c]quinoline Derivatives as Novel Potent TNF-alpha Suppressors: Synthesis and Structure—Activity Relationship of 1-, 2- and 4-Substituted 1H-imidazo[4,5-c]quinolines or 1H-imidazo[4,5-c]pyridines; Bioorganic & Medicinal Chemistry 11, 2541-2550 (2003).
Jurk, M., et al.; Human TLR7 or TLR8 independently confer responsiveness to the antiviral compound R-848, Nature Immunology, vol. 3, No. 6, p. 499 (Jun. 2002).
Moore, R.A., et al.; Imiquimod for the treatment of genital warts: a quantitative systematic review, BMC Infectious Diseases, vol. 1, No. 3, 1471-2334 (2001).
Stanley, M.A.; Imiquimod and the imidazoquinolones: mechanism of action and therapeutic potential, Clin Exp Dermatology, vol. 27 No. 7, 571-7 (Abstract) (Oct. 2002).
Sterry, W., et al.; Imiquimod 5% cream for the treatment of superficial and nodular basal cell carcinoma: radomized studies comparing low-frequency dosing with and without occlusion, British Journal of Dermatology, vol. 147, 1227-1236 (2002).
Stockfleth, E., et al.; Successful treatment of basal cell carcinomas in a nevoid basal cell carcinoma syndrome with topical 5% imiquimod, European Journal of Dermatology, vol. 12, 569-572 (2002).
van Galen, P.J., et al.; 1H-Imidazo[4,5-c]quinolin-4-amines: Novel Non-Xanthine Adenosine Antagonists, J. Med. Chem., vol. 34, 1202-1206 (1991).

* cited by examiner

*Primary Examiner*—Anna Jiang
*Assistant Examiner*—Eric S Olson
(74) *Attorney, Agent, or Firm*—Louis C. Paul

(57) ABSTRACT

The invention relates to a method and composition for treating aged or photo-damaged skin. In one embodiment, the invention includes using a composition comprising about 1% to about 2% of 1-isobutyl-1H-imidazo [4,5,-C] quinolin-4-amine in a topical preparation or cream. In further embodiments, the method includes identifying topical compositions that can diagnose or identify precancerous region of the skin, as well as methods for treating aged or photo-damaged skin by applying a Toll-like receptor activator, such as 1-isobutyl-1H-imidazo [4,5,-C] quinolin-4-amine.

21 Claims, No Drawings ized or aged skin. Biophysical and biochemical measurements can also evidence this damage, correlating changes in the content and structure of the extracellular matrix associated with the major cells of the dermis, the fibroblasts. Typically, extracellular collagen becomes highly cross-linked and inelastic, the amount of elastin is reduced, elastin is distributed differently, and there is a reduction in the amount of glycosaminoglycans. All of these factors cause the fibroblasts to become metabolically less active or quiescent and also affect the intercellular water present.

METHOD FOR TREATING DAMAGED SKIN

The invention relates to methods and compositions for treating and/or improving the appearance, function, and/or physical properties of skin. The methods can be used on skin areas that have been damaged or changed by age, exposure to ultraviolet radiation, adverse environmental pollutants, household chemicals, diseases, smoking, or malnutrition or any combination of these factors. In a particular embodiment, the invention relates to a method of treating skin by applying an effective amount of a biologically active imidazoquinoline amine product or a composition comprising the same. Specific treatment regimens are also disclosed for improving skin appearance and physiology.

DISCUSSION OF RELATED ART

Exposure to environmental factors or ultraviolet radiation can damage the visual appearance and physical properties. of skin. The appearance of fine lines and wrinkles, the loss of elasticity, the loss of firmness, the loss of consistent pigmentation, the development of telangectasias (spider veins), and coarse surface texture are all indications of damaged or aged skin. Biophysical and biochemical measurements can also evidence this damage, correlating changes in the content and structure of the extracellular matrix associated with the major cells of the dermis, the fibroblasts. Typically, extracellular collagen becomes highly cross-linked and inelastic, the amount of elastin is reduced, elastin is distributed differently, and there is a reduction in the amount of glycosaminoglycans. All of these factors cause the fibroblasts to become metabolically less active or quiescent and also affect the intercellular water present.

Although the cells of the skin have the natural ability to repair themselves and the extracellular matrix with which they are associated, age or extensive environmental damage can inhibit this regenerative ability. If quiescent fibroblasts can be metabolically activated or stimulated to divide, they will synthesize new extracellular matrix and the old, damaged matrix will be enzymatically degraded and replaced. The process of degradation and synthesis has been referred to as "dermal remodeling."

Recently, a number of products and methods have addressed the problem of aged skin by attempting to promote epidermal cell renewal or dermal remodeling. Some of the treatments to induce epidermal cell renewal include physical removal of the stratum corneum (i.e., stripping), chemical treatments (i.e., chemical peels), intense light or laser treatments, and friction (i.e., abrasive contact such as on the heels of the feet). Retinoids and the so-called hydroxy acids have also been used to induce epidermal hyperplasia at appropriate concentrations. In addition, retinoids have been used to inhibit the formation of enzymes that breakdown collagen (Matrix-metalloproteinases) and to stimulate collagen genes to produce procollagen Type 1. Damage to the stratum corneum not only sets into motion natural biochemical mechanisms to repair and replace the epidermis, but also stimulates repair and remodeling of the dermis. It has been suggested that physical or chemical changes to the stratum corneum of the skin results in epidermal basal cell replication and increases in cell renewal. If the stimulus to the stratum corneum is too great, the skin will be unable to correct the damage or will respond inappropriately to cause extensive epidermal hyperplasia, or a dry, flaky, poorly differentiated regenerated skin. On the other hand, if the damage stimulus is controlled properly, the process of dermal remodeling results in healthier, better-functioning epidermis and in skin with improved appearance and texture, greater capacity to hold moisture, and fewer surface fine lines.

Each of the currently available treatments has one or more drawbacks, such as significant skin irritation, risk for scarring, or pigmentary alterations. The applicants have surprisingly discovered a method of treatment and compositions for addressing aged and/or environmentally damaged skin without the necessity of damage to the skin or stratum corneum.

Throughout this disclosure, applicants refer to journal articles, patent documents, published references, web pages, and other sources of information. One skilled in the art can use the entire contents of any of the cited sources of information to make and use aspects of this invention. Each and every cited source of information is specifically incorporated herein by reference in its entirety. Portions of these sources may be included or added to this documents as allowed or required. However, the meaning of any term or phrase specifically defined or explained in this disclosure shall not be contradicted by the content of any source listed herein. The description and examples that follow are merely exemplary of the scope of this invention and content of this disclosure. One skilled in the art can devise and construct numerous modifications to the examples listed below without departing from the scope of this invention.

SUMMARY OF THE INVENTION

In one of its aspects, the invention includes a method of treating skin comprising topically applying to aged or damaged skin a cosmetically or dermatologically acceptable composition comprising, consisting essentially of, or consisting of 1-isobutyl-1H-imidazo [4,5,-C] quinolin-4-amine and one or more dermatologically acceptable carriers or excipients. In general, the section of the skin of the patient used for treatment can be damaged by any cause or combination of factors. The method can be used on skin areas that have been damaged or changed by age, exposure to ultraviolet radiation, adverse environmental pollutants, commonly used or household chemicals, diseases, smoking, or malnutrition or any combination of these factors. Aged and/or sun damaged, or photodamaged, skin can be most amenable to the treatment methods herein described. In one embodiment, the invention includes a treatment method wherein the skin section being treated is not being treated for viral infection at the same time. In another aspect, the invention includes a method for identifying a treatment method or treatment composition for a patient comprising applying a biologically active composition comprising an imidazoquinoline amine product and measuring the changes in skin appearance or biochemical function, wherein the patient is not being treated for viral infection at the same section of the skin. The imidazoquinolone amine product can be 1-isobutyl-1H-imidazo [4,5,-C] quinolin-4-amine, or a biologically active derivative thereof, or substance that acts on or affects a human Toll-like receptor, such as TLR7 or TLR8 (see Jurk M. et al., Nat. Immunol., 3(6):499 (2002)). Compositions, creams, suspensions, gels, and various other topical drug delivery preparations and devices are known in the art and can comprise any number of known cosmetically appropriate or dermatologically acceptable carriers, excipients, binders, or diluents (see, for example, Remington's Pharmaceutical Sciences, 20th Ed. 2000, or Remington's: The Science and Practice of Pharmacy, Mack Publishing Co.). In addition, a chemically compatible combination of one or more surfactants and one or more chelating agents can also be used in an amount effective to provide improved absorption or induce pro-inflammatory responses.

In another aspect, the invention provides a method for identifying a composition useful in improving the appearance of damaged skin on a patient, where the method includes topically applying a composition of 1-isobutyl-1H-imidazo [4,5,-C] quinolin-4-amine and a dermatologically acceptable carrier or excipient to a section of the skin of the patient. The section of skin can be monitored by a number of available assays or techniques, for example visual or microscopic inspection, and changes in the skin appearance or biochemical function can be measured. In a preferred embodiment, the patient is not being treated for viral infection or skin cancer at the same section of the skin. In this and other embodiments, the composition can be applied daily, weekly, monthly, multiple times a day, or multiple times a week. The composition may contain different concentrations of a biologically active product that can function to induce a pro-inflammatory response in the skin, such as about 5% of 1-isobutyl-1H-imidazo [4,5,-C] quinolin-4-amine, or about 0.1% to about 10%, or any range in between, such as about 1.0% to about 1.5%. For example, one treatment regimen is a daily application of about a pea-sized amount of about 1.25% cosmetic cream composition of 1-isobutyl-1H-imidazo [4,5,-C] quinolin-4-amine, or approximately 1% to about 2%, or about 1.5% to about 2%. Alternatively, a once every other day, or once every third day, or twice a week application of an approximately 5% composition can be selected and used. As noted, the methods of the invention can be especially effective on aged or photo-damaged skin and/or skin containing fine lines or clinical wrinkles characteristic of aged skin.

In another aspect, the invention includes a method for treating aged or sun or photo-damaged skin comprising topically applying an effective amount of a composition consisting essentially of 1isobutyl-1H-imidazo [4,5,-C] quinolin-4-amine or a biologically active derivative thereof and a dermatologically acceptable carrier or excipient to a section of the skin of the patient exhibiting clinical wrinkles or photo-damage. In a preferred embodiment, the patient is not being treated for viral infection or skin cancer at the same section of the skin. The composition can be applied daily, weekly, monthly, multiple times a day, or multiple times a week, and the concentration of 1-isobutyl-1H-imidazo [4,5,-C] quinolin-4-amine, or derivative thereof, can vary as above.

In another aspect, the invention includes a method of inducing an immune cytotoxic response in a section of damaged dermal or epidermal tissue of a patient comprising topically applying an effective amount of a cosmetically or dermatologically acceptable composition comprising a immunomodulatory compound capable of attracting macrophage cells to the area surrounding the section of tissue. As known in the art, imiquimod or 1-isobutyl-1H-imidazo [4,5,-C] quinolin-4-amine can function to attract macrophage and other immune cells to induce a pro-inflammatory response. In addition, imiquimod is thought to interact with the Toll-like receptor 7 (TLR7) and signal the production of IFN-$\alpha$, TNF-$\alpha$, and/or IL-12. Thus, other immunomodulatory products, compositions, and suspensions with similar biological function can also be used or tested in the methods of this invention and many such products are known in the art. For example, products that induce IFN-$\alpha$, TNF-$\alpha$, and/or IL-12 production can be selected in place of imiquimod or in addition to imiquimod.

In general, the section of dermal or epidermal tissue that is treated exhibits an improved appearance or improved physiological properties following the application of the composition after a period of 4 weeks, 8 weeks, 16 weeks, 20 weeks, or 24 weeks.

In another aspect, the methods of the invention include treating skin with a composition of 1-isobutyl-1H-imidazo [4,5,-C] quinolin-4-amine, or a derivative thereof, in order to diagnose or identify areas of skin containing precancerous lesions or keratinocyte dysplasia. As above, the treatment regimen, application frequency, and concentration can vary.

Additional aspects of the invention will be set forth in part in the following description and in part will be apparent from the description or may be learned by practice of the invention. The purposes and features of the invention will be realized and attained by means of the elements and combinations particularly pointed out in the appended claims. Further features of the invention will be set forth in part in the description that follows and in part will be apparent from the description, or may be learned by practice of the invention. Neither the description here nor the examples given should be taken as a limitation of the scope of the invention.

DETAILED DESCRIPTION

The present invention provides a novel method of treatment and a novel composition for treating aged and/or environmentally damaged or deteriorated skin. In general the present invention includes a method of treating skin comprising topically applying to damaged skin a cosmetic composition in an amount effective to provide increased replacement of skin cells, advantageously causing replacement and remodeling of the stratum corneum, epidermis, and/or dermis of the skin and improvements in the appearance, function, and physiological properties of the skin. While not bound by any particular theory of how the invention works, the skin improving properties of the present invention can be associated with the immunomodulatory mechanisms of the imidazoquinolone amine product. These products or derivatives of them activate macrophages and other cells that induce pro-inflammatory cytokines, typically one or more interferons, interferon-alpha, TNF, and/or interleukin-12. The cytotoxic action resulting from the presence of these cytokines effectively destroys damaged areas and induces regeneration of the skin. Selecting a topical treatment regimen and concentration of immunomodulatory product that beneficially induces this pro-inflammatory response effectively improves the appearance and physiology of sun damaged, aged, and/or environmentally damaged skin. In a more general aspect, the invention also includes a method for analyzing the skin improving properties of a composition comprising any immunomodulatory product, or combination of immunomodulatory products, or any immune-cytotoxic product capable of being applied topically, comprising topically applying the composition and measuring the beneficial effect on skin. In general, these products act by recruiting macrophages and/or other immune cells to a particular site in order to initiate the cell-cytotoxic immune reaction. One of skill in the art is familiar with numerous products that can act as immunomodulatory agents or agents that promote an immune-cytotoxic response in skin cell or the layers of the dermis. These products and combinations of these products can be also be analyzed in this way.

The methods for measuring the effect on skin can be any one or more of those commonly used in the art. For practical reasons, the most amenable measurement is visual or microscopic inspection. Fine lines, dry or flaking dermis, and/or hardened textures can all be easily monitored by visual or microscopic inspection. In addition, tissue samples can generate water retention abilities and biochemical assays for particular concentrations of extracellular matrix proteins or pro-inflammatory cells.

A preferred imidazoquinoline amine product for use in the treatment methods or other aspects of the invention is the available 1-isobutyl-1H-imidazo [4,5,-C] quinolin-4-amine or 4-Amino-1-isobutyl-1H-imidazo[4,5,c] quinolone (Aldara™ or imiquimod, 3M Pharmaceuticals) shown below (Formula A).

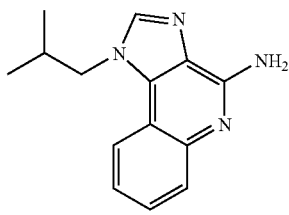

Formula A

4-Amino-1-isobutyl-1H-imidazo[4,5-c]quinoline

This product has previously been used to treat genital warts (see Moore et al., Biomedical Central Infect. Diseas. 1:3 (2001) www.biomedicalcentral.com/1471-2334/1/3, incorporated herein by reference) and to treat skin cancer. However, no beneficial effects on photo-damaged or aged skin has been reported. Preferably, a composition for treatment comprises 1%, or between about 1% and about 5%, or between about 1% and about 3% of 1-isobutyl-1H-imidazo [4,5,-C] quinolin-4-amine. Higher concentrations, of about 5% to about 10%, or lower concentrations, of about 0.1% to about 1%, can also be selected for use. Any of these concentrations can be combined with any one or more of the treatment regimens, which can be daily application, every other day application, three times a week application, or five days a week application, for example. For certain treatments, the application can be up to 24 hour a day or several applications a day until benefits or improvements are measurable. Treatment periods can be from 4 to 8 weeks, 8 to 16 weeks, or longer or can be monitored each application. In a preferred treatment method, a 5% concentration is selected and used with a four times a day application regimen, or a 1.25% concentration is elected for daily application. Typically, the skin being treated does not have a viral infection, such as the appearance of genital warts or presence of papillomavirus infection. Alternatively, the skin being treated does not have a skin cancer lesion or a combination of skin cancer and viral infection.

In addition, derivatives of 1-isobutyl-1H-imidazo [4,5,-C] quinolin-4amine can be selected for use under the same concentration and regimens discussed above. In one particular derivative possible, the product is defined by the formula below (Formula B),

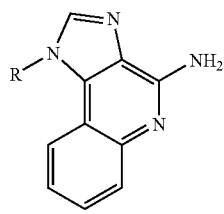

Formula B where the R group can be a C1-C10 alkane group, branched alkane, substituted alkane, or branched substituted alkane. Additional derivatives can add substitution on the amine group, for example. A number of possible derivatives are found in U.S. Pat. No. 4,689,338, Izumi et al., Bioorg. Med. Chem. 11(12):2541-50 (2003), and van Galen et al., J. Med. Chem. 34(3):1202-6 (1991), which are specifically incorporated herein by reference in their entirety.

In a first example of a method of the invention, a 5% imiquimod composition is applied to Patient A skin. After 8 weeks of daily application, the appearance of clinical wrinkles by visual inspection decreases and the skin has a generally improved and healthier appearance with the most noticeable improvement being in pigmentation and texture.

In a further example of a method of the invention, Patient B is treated with a pea size aliquot of 5% imiquimod every day to the entire face. Areas of the skin with precancerous lesions on the nose became very red, eroded and irritated. A biopsy demostrates the presence of BCC (basal cell carcinoma) in precancerous regions. The non-precancerous skin (normal, photodamaged skin) does not become irritated but looks smoother, with more regular pigmentation, and improvement of the fine wrinkles.

One skilled in the art is familiar with many methods and techniques for evaluating or monitoring changes in the skin. Visual and photographic examination and assessment is commonly used to show or demonstrate changes in skin. For example, changes in pigmentation, texture, and the presence of wrinkles or fine lines can all be monitored through visual assessment. In addition, a mexameter can be used to measure skin pigment, a tewameter and/or evaporometer can be used to measure water content, a laser doppler device can measure blood flow, and a visioscan or optical profilometer can measure surface texture, wrinkles, and/or roughness. Any one or any combination of these methods can be used, in particular, to measure, monitor, or detect changes in fine wrinkles, mottled hyperpigmentation, tactile roughness, lentigines, course or deep wrinkles, telangiectasia, skin laxity, keratinocytic atypia, melanocytic atypia, and/or dermal elastosis. Thus, the methods and composition of the invention can be used to treat and/or to evaluate possible treatment compositions where any one of these diseases or conditions are present or may be present.

Though the invention has been described and exemplified above, nothing in this specification should be taken as a limitation of the scope of the invention to any particular embodiment, preferred embodiment, or example.

What is claimed is:

1. A method for treating fine lines or clinical wrinkles on a section of aged skin or non-precancerous, normal photodamaged skin, said section of skin not being treated for viral infection or skin cancer, comprising topically applying an effective amount of a composition consisting essentially of
   (a) an imidazoquinoline amine derivative conforming to the structure

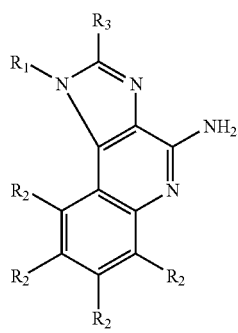

wherein
(i) $R_1$ is selected from the group consisting of $C_1$-$C_{10}$ alkyl;
$C_1$-$C_6$ hydroxylalkyl; and acyloxyalkyl wherein the acyloxy moiety is $C_2$-$C_4$ alkanoyloxy or benzoyloxy, and the alkyl moiety contains one to six carbon atoms or a benzyl, (phenyl)ethyl or phenyl substituent;

(ii) $R_2$ is hydrogen or no more than two non-hydrogen moieties selected from the group consisting of $C_1$-$C_4$alkyl, $C_1$-$C_4$ alkoxy, and halogen with the proviso that non-hydrogen moieties are present then said moieties together contain no more than 6 carbon atoms;

(iii) $R_3$ is selected from the group consisting of hydrogen, $C_1$-$C_8$alkyl, benzyl, (phenyl)ethyl and phenyl; and (b) a dermatologically acceptable carrier or excipient to a section of the skin of a patient exhibiting fine lines, clinical wrinkles or non-precancerous, normal photodamage, wherein the patient is not being treated for viral infection or skin cancer at the same section of the skin.

2. The method of claim 1, wherein the composition is applied daily.

3. The method of claim 1, wherein the imidazoquinoline amine derivative is 1-isobutyl-1H-imidazo [4,5-c] quinolin-4-amine, said derivative being present at a concentration of up to about 5% by weight of the total composition.

4. The method of claim 1, wherein the composition is applied one or more times a week.

5. The method of claim 1, wherein the composition consists essentially of about 1% to about 2% of 1-isobutyl-1H-imidazo [4,5-c] quinolin-4-amine.

6. The method of claim 1, wherein the composition consists essentially of about 1% to about 2% of 1-isobutyl-1H-imidazo [4,5-c] quinolin-4amine and is applied daily.

7. The method of claim 1, wherein the composition consists essentially of about 1% to about 2% of 1-isobutyl-1H-imidazo [4,5-c] quinolin-4-amine and is applied one or more times a week and less than once a day.

8. The method of claim 1, wherein the composition consists essentially of about 1.25% of 1-isobutyl-1H-imidazo [4,5-c] quinolin-4-amine and is applied daily.

9. The method of claim 1, wherein measuring the changes in skin appearance is performed by visual, photographic, or microscopic assessment or inspection of the skin.

10. A method of inducing an immune cytotoxic response in a section of normal photodamaged dermal or epidermal tissue of a patient exhibiting fine lines and clinical wrinkles, said section of tissue not being treated for viral infection or skin cancer, comprising topically applying an effective amount of a cosmetically or dermatologically acceptable composition comprising an immunomodulatory compound capable of attracting macrophage cells to the area surrounding the section of tissue exhibiting fine lines and clinical wrinkles, said immunomodulatory compound conforming to the structure

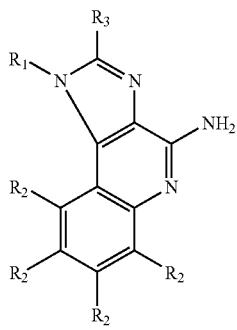

wherein
(i) $R_1$ is selected from the group consisting of $C_1$-$C_{10}$ alkyl; $C_1$-$C_6$ hydroxylalkyl; and acyloxyalkyl wherein the acyloxy moiety is $C_2$-$C_4$ alkanoyloxy or benzoyloxy, and the alkyl moiety contains one to six carbon atoms or a benzyl, (phenyl)ethyl or phenyl substituent;

(ii) $R_2$ is hydrogen or no more than two non-hydrogen moieties selected from the group consisting of $C_1$-$C_4$alkyl, $C_1$-$C_4$ alkoxy, and halogen with the proviso that non-hydrogen moieties are present then said moieties together contain no more than 6 carbon atoms;

(iii) $R_3$ is selected from the group consisting of hydrogen, $C_1$-$C_8$alkyl, benzyl, (phenyl)ethyl and phenyl;

whereby the section of tissue exhibits improved appearance or physiological properties following the application of the composition after a period of at least 4 weeks.

11. The method of claim 10, wherein a Toll-like receptor 7 is activated by the action of the immunomodulatory compound.

12. A method for identifying a precancerous region of skin comprising topically applying to a region of skin exhibiting fine lines and clinical wrinkles a composition comprising 1-isobutyl-1H-imidazo [4,5-c]quinolin-4-amine and monitoring the physical appearance of the region of skin exhibiting fine lines and clinical wrinkles, whereby a precancerous region becomes inflamed or irritated following application of the composition.

13. The method of claim 12 wherein the composition is applied daily.

14. The method of claim 13 wherein the composition comprises about 1% to about 2% of 1-isobutyl-1H-imidazo [4,5-c] quinolin-4-amine.

15. The method of claim 1, wherein one or both of the $R_1$ and $R_3$ substituents on the imidazoquinoline amine derivative is a benzyl, (phenyl)ethyl or phenyl group, and the benzene ring on said group contains one or two moieties independently selected from the group consisting of $C_1$-$C_4$ alkyl, $C_1$-$C_4$ alkoxy and halogen, with the proviso that if the benzene ring is substituted by two of said moieties, then said moieties together contain no more than six carbon atoms.

16. A method for treating fine lines or clinical wrinkles on a section of aged skin or non-precancerous, normal photodamaged skin, comprising topically applying an effective amount of a composition consisting essentially of (a) an imidazoquinoline amine derivative conforming to the structure

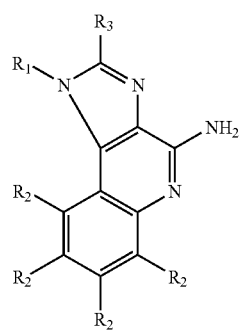

wherein
$R_1$ is selected from the group consisting of $C_1$-$C_{10}$ alkyl; $C_1$-$C_6$ hydroxylalkyl; and acyloxyalkyl wherein the acyloxy moiety is $C_2$-$C_4$alkanoyloxy or benzoyloxy, and the alkyl moiety contains one to six carbon atoms or a benzyl, (phenyl)ethyl or phenyl substituent; and (b) a dermatologically acceptable carrier or excipient to a section of the skin of a patient exhibiting fine lines, clinical wrinkles or non-precancerous, normal photodamage photo-damage, wherein the patient is not being treated for viral infection or skin cancer at the same section of the skin.

17. The method of claim 16, wherein the $R_1$ substituent on the imidazoquinoline amine derivative is a benzyl, (phenyl) ethyl or phenyl group, and the benzene ring on said group contains one or two moieties independently selected from the group consisting of $C_1$-$C_4$ alkyl, $C_1$-$C_4$ alkoxy and halogen, with the proviso that if the benzene ring is substituted by two of said moieties, then said moieties together contain no more than six carbon atoms.

18. The method of claim 1, wherein the composition is applied twice-daily.

19. The method of claim 18 wherein the composition consisting essentially of from about 1% to about 2% of 1-isobutyl-1H-imidazo [4,5-c] quinolin-4-amine is applied twice daily to the skin of a patient.

20. The method of claim 1, wherein the composition is applied three-times daily.

21. The method of claim 1, wherein the composition is applied four-times daily.

* * * * *